(12) United States Patent
Karhanek et al.

(10) Patent No.: US 11,940,410 B2
(45) Date of Patent: *Mar. 26, 2024

(54) FUNCTIONALIZED NANOPIPETTE BIOSENSOR

(71) Applicant: The Regents of the University of California, Oakland, CA (US)

(72) Inventors: Miloslav Karhanek, Santa Cruz, CA (US); Chris David Webb, Watsonville, CA (US); Senkei Umehara, Tokyo (JP); Nader Pourmand, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 17/578,151

(22) Filed: Jan. 18, 2022

(65) Prior Publication Data

US 2022/0260520 A1    Aug. 18, 2022

Related U.S. Application Data

(63) Continuation of application No. 16/588,326, filed on Sep. 30, 2019, now Pat. No. 11,255,814, which is a
(Continued)

(51) Int. Cl.
*G01N 27/42* (2006.01)
*G01N 27/403* (2006.01)
*G01N 33/487* (2006.01)

(52) U.S. Cl.
CPC ......... *G01N 27/42* (2013.01); *G01N 27/4035* (2013.01); *G01N 33/48707* (2013.01)

(58) Field of Classification Search
None
See application file for complete search history.

(56) References Cited

U.S. PATENT DOCUMENTS 4,478,946 A   10/1984   Van der Merwe et al.
4,539,061 A   9/1985    Sagiv
(Continued)

FOREIGN PATENT DOCUMENTS

EP       0324867        7/1989

OTHER PUBLICATIONS

Butler, et al., "Ionic Current Blockades from DNA and RNA Molecules in the alpha-Hemolysin Nanopore," Biophysical Journal, vol. 93, 3229-3240.
(Continued)

*Primary Examiner* — J. Christopher Ball
(74) *Attorney, Agent, or Firm* — Bozicevic, Field & Francis LLP; Shweta Chandra

(57) ABSTRACT

Disclosed are methods and devices for biomolecular detection, comprising a nanopipette, exemplified as a hollow inert, non-biological structure with a conical tip opening of nanoscale dimensions, suitable for holding an electrolyte solution which may contain an analyte such as a protein biomolecule to be detected as it is passed through the tip opening. Biomolecules are detected by specific reaction with peptide ligands chemically immobilized in the vicinity of the tip. Analytes which bind to the ligands cause a detectible change in ionic current. A sensitive detection circuit, using a feedback amplifier circuit, and alternating voltages is further disclosed. Detection of IL-10 at a concentration of 4 ng/ml is also disclosed, as is detection of VEGF.

13 Claims, 9 Drawing Sheets

Related U.S. Application Data continuation of application No. 16/298,232, filed on Mar. 11, 2019, now abandoned, which is a continuation of application No. 15/697,289, filed on Sep. 6, 2017, now abandoned, which is a continuation of application No. 14/603,134, filed on Jan. 22, 2015, now Pat. No. 9,766,204, which is a continuation of application No. 12/435,056, filed on May 4, 2009, now Pat. No. 8,940,142.

(60) Provisional application No. 61/126,644, filed on May 5, 2008.

(56) References Cited

U.S. PATENT DOCUMENTS

| | | | |
|---|---|---|---|
| 4,562,157 | A | 12/1985 | Lowe et al. |
| 5,077,210 | A | 12/1991 | Eigler et al. |
| 5,091,513 | A | 2/1992 | Huston et al. |
| 5,132,405 | A | 7/1992 | Huston et al. |
| 5,985,121 | A | 11/1999 | Wu et al. |
| 8,940,142 | B2 * | 1/2015 | Karhanek ........ G01N 27/4035 205/792 |
| 2002/0015952 | A1 | 2/2002 | Anderson et al. |
| 2002/0144905 | A1 | 10/2002 | Schmidt |
| 2005/0074778 | A1 | 4/2005 | Letant et al. |
| 2006/0083781 | A1 | 4/2006 | Shastri et al. |
| 2006/0120961 | A1 | 6/2006 | Schneider et al. |
| 2006/0219558 | A1 | 10/2006 | Hafeman et al. |
| 2008/0025875 | A1 | 1/2008 | Martin et al. |

OTHER PUBLICATIONS

Churbanov, et al., "Duration learning for analysis of nanopore ionic current blockades," Fourth Annual MCBIOS Conference, Computational Frontiers in Biomedicine, New Orleans, LA, Feb. 1-3, 2007, published Nov. 2007.

Drummond, et al., "Electrochemical DNA sensors," Nature Biotechnology, Oct. 2003, pp. 1192-1199, vol. 21, No. 10.

Fologea, et al., "Electrical characterization of protein molecules by a solid-state nanopore," Appl. Phys. Lett., Jul. 2007, 91:053901.

Guangfen, et al., "A new method of preparing fiber-optic DNA biosensor and its array for gene detection," Science in China (Series C), Feb. 2001, vol. 44, No. 1, 33-39.

Karhanek, et al., "Single DNA Molecule Detection Using Nanopipettes and Nanoparticles," Nano Letters, Jan. 25, 2005, vol. 5, No. 2, 403-407.

Saleh, et al., "Direct detection of antibody-antigen binding using an on-chip artificial pore," PNAS, Feb. 4, 2003, vol. 100, No. 3, 820-824.

Umehara, et al., "Label-free biosensing with functionalized nanopipette probes," PNAS Early Edition, Mar. 24, 2009, vol. 106, No. 12, 4611-4616.

Umehara, et al., "Current Rectification with Poly-L-Lysine-Coated Quartz Nanopipettes," Nano Letters, 2006, pp. 2486-2492, vol. 6, No. 11.

Youngseon, et al., "Biosensing with conically shaped nanopores and nanotubes," Physical Chemistry Chemical Physics, 2006, pp. 4976-4988, No. 8.

* cited by examiner

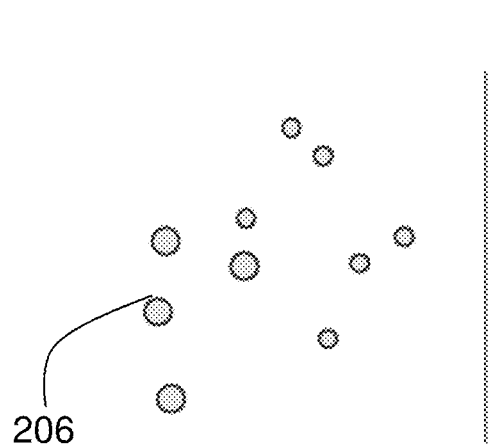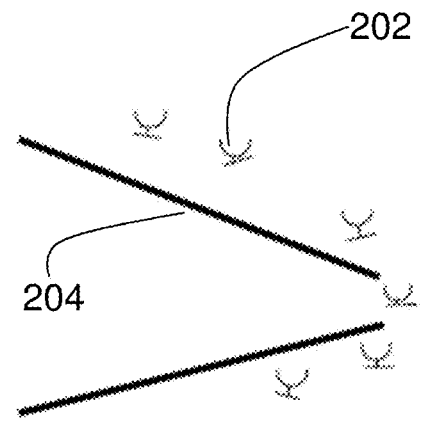
Fig. 2A Fig. 2B
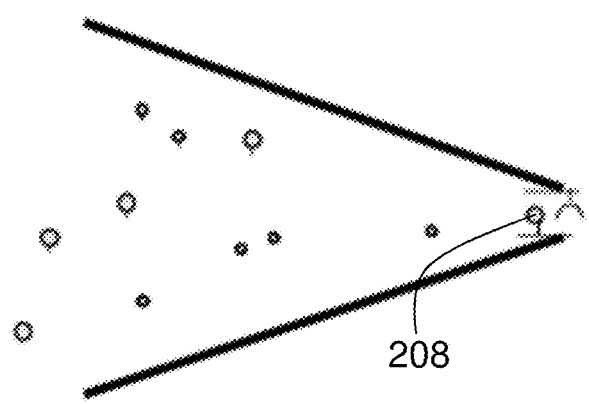
Fig. 2C

FUNCTIONALIZED NANOPIPETTE BIOSENSOR

CROSS-REFERENCE TO RELATED APPLICATIONS

This application is a continuation of U.S. patent application Ser. No. 16/588,326, filed on Sep. 30, 2019, which is a continuation of U.S. patent application Ser. No. 16/298,232, filed on Mar. 11, 2019, which is a continuation of U.S. patent application Ser. No. 15/697,289 filed Sep. 6, 2017, which is a continuation of U.S. patent application Ser. No. 14/603,134 filed Jan. 22, 2015, now U.S. Pat. No. 9,766,204 issued Sep. 19, 2017, which is a continuation of U.S. patent application Ser. No. 12/435,056 filed May 4, 2009, now U.S. Pat. No. 8,940,142 issued Jan. 27, 2015, which claims priority from U.S. Provisional Patent Application No. 61/126,644, filed May 5, 2008, the disclosures of which are hereby incorporated by reference in their entireties.

STATEMENT OF GOVERNMENTAL SUPPORT

This invention was made with government support under NIH Grant P01-HG000205 and NSF Grant DBI0830141. The government has certain rights in the invention.

BACKGROUND OF THE INVENTION

Field of the Invention

The present invention relates to the field of biomolecule sensing and sensors, the sensors having channels with tips having nanoscale openings.

Related Art

Presented below is background information on certain aspects of the present invention as they may relate to technical features referred to in the detailed description, but not necessarily described in detail. That is, certain components of the present invention may be described in greater detail in the materials discussed below. The discussion below should not be construed as an admission as to the relevance of the information to the claimed invention or the prior art effect of the material described.

Several groups are developing single-molecule detection methods using a nanopore (Deamer and Akeson, 2000; Deamer and Branton, 2002; Li et al., 2003). The first efforts in this field used an ion-channel protein to form the nanopore, and the ionic current through the pore was measured. The first reported success was the ability to detect single oligonucleotides moving through the pore due to the blockage of ionic current while the oligonucleotide traveled through the nanopore (Kasianowicz et al., 1996). This overcomes the common molecular diagnostics drawback of requiring multiple copies of the analyte, since single molecules were detectable. The ultimate goal of these efforts is to discriminate individual nucleotides in a DNA molecule based on differential blockage of the ionic current.

SPECIFIC PATENTS AND PUBLICATIONS

Karhanek M., Kemp J. T., Pourmand N., Davis R. W. and Webb C. D, "Single DNA molecule detection using nanopipettes and nanoparticles," *Nano Lett.* 2005 February; 5(2): 403-7 discloses that single DNA molecules labeled with nanoparticles can be detected by blockades of ionic current as they are translocated through a nanopipette tip formed by a pulled glass capillary. The disclosed set up uses a voltage clamp circuit, which utilized a single detecting electrode in a bath to detect nanoparticle-DNA current block.

Ying et al., "The scanned nanopipette: a new tool for high resolution bioimaging and controlled deposition of biomolecules," *Phys. Chem. Chem. Phys.*, 2005, 7, 2859-2866, DOI: 10.1039/b506743j, disclose a nanopipette which can also be used for controlled local voltage-driven application of reagents or biomolecules and this can be used for controlled deposition and the local delivery of probes for mapping of specific species.

Umehara et al., "Current Rectification with Poly-L-lysine Coated Quartz nanopipettes," *Nano Lett.* 6(11):2486-2492 (2006) discloses current responses of noncoated and Poly-l-lysine coated nanopipettes using a nanopipette in a bath solution.

Umehara et al., "Label-free biosensing with functionalized nanopipette probes," *Proc. Nat Acad. Sci.* 106(12): 4611-4616 (Mar. 24, 2009), published after the provisional filing date, discloses certain aspects of work described below and is specifically incorporated herein (along with other references cited here) for description desired for a fuller understanding of aspects of the present invention disclosed there.

BRIEF SUMMARY OF THE INVENTION

The following brief summary is not intended to include all features and aspects of the present invention, nor does it imply that the invention must include all features and aspects discussed in this summary.

In certain aspects, the present invention comprises a device for specific detection of an analyte in a sample containing electrolyte, said device comprising a nanopipette having a tip with a nanoscale opening between an interior of the nanopipette and an external area for contacting the sample, said nanopipette defining an internal volume communicating with the sample. The internal volume will contain electrolyte, and the sample will contain electrolyte. The purpose of the electrolyte is to provide a source of ions for ionic current flow. The nanoscale opening may be on the order of 10-100 nm, typically 50 nm, and the opening is sized so that binding of an analyte in or near the opening will impede current flow, even if only one or a few molecules are bound. Blocking by specific binding of an analyte causes a reduction of ionic current flow through the electrolyte solution. Thus, the tip has chemically attached thereto, in the vicinity of the opening, a peptide-binding molecule specifically binding to the analyte in the sample. The chemical attachment preferably includes a covalent linkage, through a variety of pre-layers attached to the quartz nanopipette; as a final step, a binding molecule, such as one comprising protein A, which specifically and tightly binds the Fc portion of antibodies, may be used. The device of the invention further comprises a first electrode, arranged to be in contact with electrolyte in the interior of the nanopipette. The electrolyte is part of, or is added to the sample; the sample inherently contains the analyte to be detected. The sample may also be modified to contain various controls, or analyte modifying materials, although no analyte label is needed, and no inert or other larger particle is attached to the analyte molecules. Analyte in the vicinity of the opening is captured by the peptide binding ligand, as the tip of the nanopipette is in contact with sample containing analyte. The first electrode, in the electrolyte interior of the nanopipette, is further arranged to be connected to an amplifier input in a current detecting circuit. The device further comprises a second electrode, arranged to be in contact with the electrolyte, and the second electrode is exterior of the nanopipette, and further arranged for connection to the current detecting circuit, whereby electrolyte in the interior of the nanopipette and electrolyte in the bath permits ionic current to flow between the electrodes and through the tip, said ionic current being detectibly reduced when the tip is blocked by analyte.

As an example of use of the present device, a peptide binding ligand attached at the opening of the tip will bind specifically to the corresponding receptor (e.g., antigen enzyme, small molecule or metabolite). This technology can have a great impact in many areas including basic research, health care, environmental monitoring, and homeland defense.

Thus the present invention, in certain aspects, may be used to detect and uniquely identify biological markers, pathogens, or contaminants without the need to label or pre-process them. They are identified by their differential blockage events of the ionic current while passing through a functionalized nanopipette. As an example, cancer biomarkers which may be present in serum are measured.

The present invention, in certain aspects, may also be used to detect various protein molecules and protein metabolites by detecting and analyzing current blockage events resulting from binding to the molecules' counterparts (ligands) which are attached to the nanopipette tip. Blockage events can represent not only permanent binding events of the target molecule to the probe molecule but also conformational changes of the final molecular complex.

The present invention, in certain aspects, may also be used to distinguish between various molecules passing through the nanopipette and creating characteristic blockage events. Statistical or pattern recognition analysis of these events produces parameters which are used in identification of target molecules. For example, statistical analysis is described in Butler et al., "Ionic Current Blockades from DNA and RNA Molecules in the α-Hemolysin Nanopore," Biophys J. 2007 Nov. 1; 93(9): 3229-3240.

The present invention, in certain aspects, may also be used to use nanopipette tips coated with various agents to enable and improve detection of various molecules. Coating of the nanopipette tip creates better resolution of the nanopipette by appropriate adjustment of its size and surface chemistry for particular target molecules. Coating is also used to enable and create conditions for surface attachment of probe molecules capturing target molecules.

BRIEF DESCRIPTION OF THE DRAWINGS

FIG. 2A, 2B and 2C is a series of schematic drawings showing methods used in attaching antibodies or other peptide ligands to a nanopipette surface such that the ligands are in the vicinity of the tip opening.

FIG. 5 is a graph showing nanopipette current response comparing anti-IL-10 IgG treated pipette with a control, anti-ferritin, showing current changes detectible upon binding of IL-10 to antibodies on the nanopipette. Lines 402 and 408 are from antiferritin; line 404 shows a current reduction trace and line 406 shows a current increase trace resulting from anti-IL10 interaction with IL-10.

FIG. 6 is a graph of an experiment numbered 080122, using anti-VEGF antibody binding to VEGF. It shows lines connecting peaks and the current change over time after adding VEGF.

FIG. 7 is a similar graph from experiment numbered 080205, which used anti-IL10 antibody binding to IL-10. It showed a big change in the negative ion current response and a small but significant change in the positive ion current response for the anti-human IL-10 IgG functionalized nanopipette.

FIG. 8 is a graph showing results from a limit of detection experiment, numbered experiment 080224. Addition of analyte at different concentrations is shown.

DETAILED DESCRIPTION OF THE PREFERRED EMBODIMENT

Overview

Figure 1:
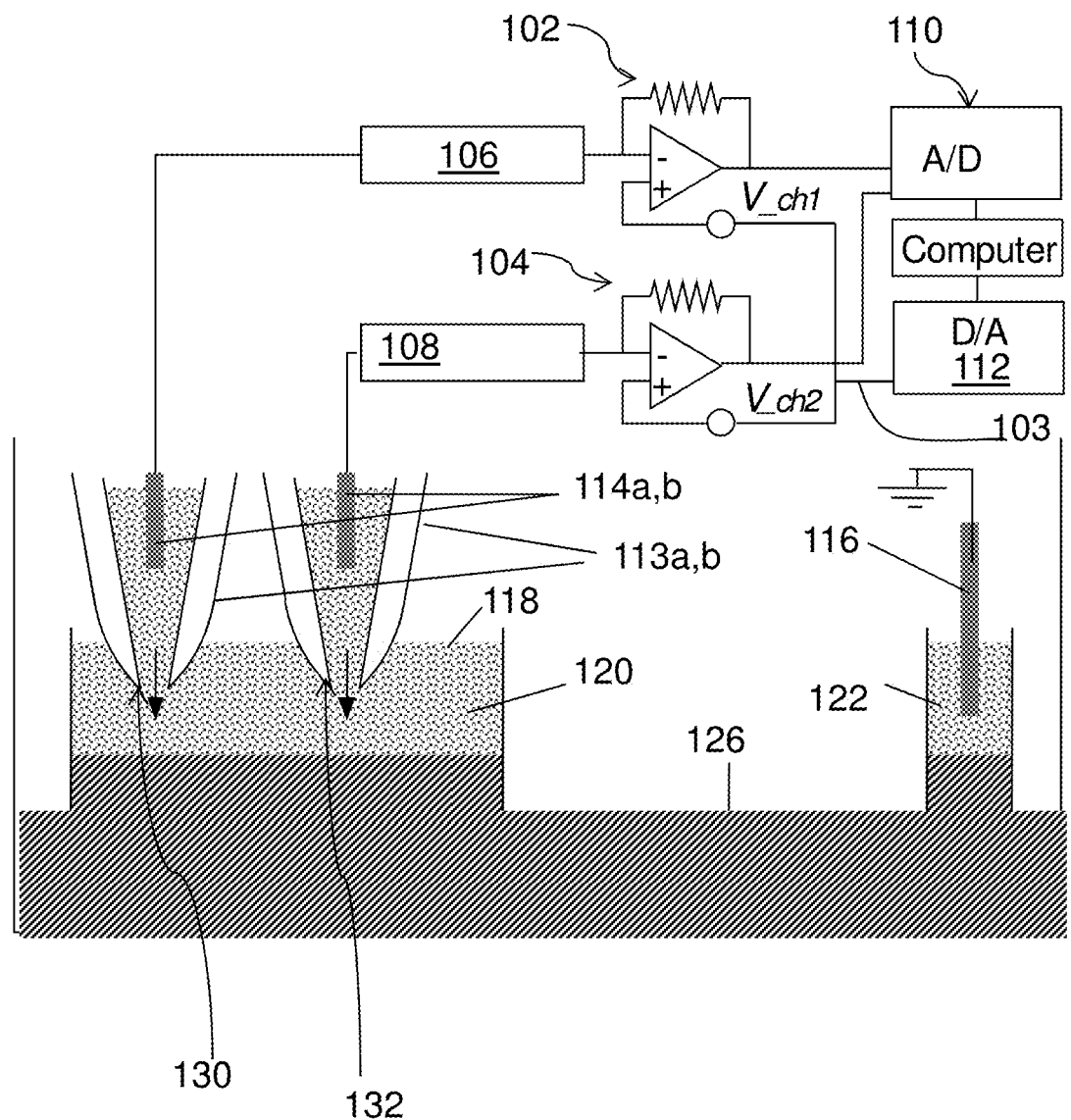
FIG. 1 is a schematic diagram of an apparatus containing functionalized Axopatch voltage-clamp experiment diagram, showing two voltage channels, V_ch1 and V_ch2. In addition, two currents will flow through the tip regions of the nanopipettes, I-ch1, in the vicinity of tip 130, and I_ch2, in the vicinity of tip 132.

The present methods and devices are directed to nanopipettes which have been chemically modified in their tip areas to contain a peptide ligand which may be used for rapid and sensitive detection of antigens in a sample. One application of this technology is a point-of-care diagnostic device that can test a patient's sample for the presence of specific known pathogens and determine the proper course of treatment. This can also be useful for current research applications that use ELISA or protein microarrays for readout. The present methods do not require that the analyte be labeled or attached to a nanoparticle to increase blocking ability. No pretreatment of the sample is required. Alternatively, an assay similar to ELISA could be performed with this system, except that the colorimetric or fluorescent readout would be replaced with nanoparticle labels. Of course, the nanochannel (inner diameter of the nanopipette) and size of the particles would be scaled accordingly to result in the appropriate detectable signals. In this example, antibodies could be labeled with differently-sized nanoparticles. The bound and unbound antibodies would be detected by the length of the ionic block, with a longer block resulting with an antibody bound to a large protein. A very quantitative ELISA-like assay would result, since individual molecules would be analyzed.

An additional application would be the analysis of nanoparticle syntheses. Several groups are developing processes to synthesize nanoparticles with different materials for many different applications (Sun and Murray, 2000; Peng et al., 2000; Puntes et al., 2001). The analysis of such syntheses is labor intensive, involving the imaging of synthesized products with an electron microscope. The electron micrographs are then analyzed for determining the size and uniformity of the synthesis. The system proposed in this effort would rapidly analyze nanoparticles, with the size being determined by the amount of ionic current blocked.

Devices according to the present invention may also involve protein-based detection. The ability to perform sensitive, real-time, and cost effective proteome analysis is of crucial value in clinical diagnostics, academic research, and drug development. Described below is an electrical-based, nanopipette biosensor with the ability to carry out biomolecule detection. The present immunoanalytical method based on antibody-antigen interaction has a specific nature and adaptability. The surface chemistry's proof-of-principal was made in a glass slide model system and subsequently implemented to the nanopipette biosensor. In repeated voltage clamp experiments the nanopipette biosensors proved to specifically detect antigen cancer marker molecules VEGF and IL-10, at a concentration of 4 µg/mL. Nanopipette biosensor limit of detection remains unknown but it is believed to be <4 ng/mL.

Compared to ELISA, nanopipette biosensors could have several potential advantages. The use of enzymes and other detection agents are not necessary with nanopipette biosensors, which make the technology less expensive and more sensitive. With nanopipette biosensors we measure antigen-antibody real-time binding events and because of the computer interface, more comprehensive data for more than just quantitative analysis can be collected.

The fact that nanopipette biosensor detection is done in real-time could make it an attractive diagnostic tool since it might allow close to instantaneously patient bedside analysis with little waiting time for diagnostic results. With the nanopipette platform we have shown specific binding on one pipette with successful negative control on another in the same sample bath, hence nanopipette multiplexing could be implemented. Verification of specific binding with different negative controls is also desirable. Of high interest is determination of nanopipette biosensor limit of detection, both for clean target molecule sample and for target molecule in plasma. Also, to re-use the nanopipettes for other antibodies or more experiments is possible, given that one could alter the pH (elution buffer could be used) or rinse the nanopipettes in high salt buffers. This method has been proven to work in Protein A/G affinity chromatography.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "nanopipette" means a hollow self-supporting, inert, non-biological structure with a conical tip opening of nanoscale, i.e., 0.05 nm to about 500 nm, preferably about (+ or −20%) 50 nm. The hollow structure may be glass or quartz, and is suitable for holding inside of it a fluid which is passed through the tip opening. The interior of the nanopipette is selected or modified to minimize nonspecific binding of analyte. The interior is sized to allow insertion of an electrode that contacts solution in the nanopipette.

The term "ionic current" means an electric current which flows through an electrolyte material, such as salts or buffer in solution in a polymer, etc., which provides an ionically conductive medium, as opposed to an electronic current flow such as electrons in a wire. The ionic current is carried by a flow of charged ions, such as in an electrolyte solution.

The term "analyte" is used in a conventional sense and in conjunction with the phrase "analyte binding molecule," or ligand (to the analyte). The term "analyte" is used herein broadly to refer to any substance to be analyzed, detected, measured, or labeled. Examples of analytes include, but are not limited to: proteins, peptides, hormones, haptens, antigens, antibodies, receptors, enzymes, nucleic acids (DNA and RNA), polysaccharides, chemicals, polymers, viruses, prions, toxins, organic drugs, inorganic drugs, allergens, pollutants and nanoscale combinations thereof. It will be understood that detection of, for example, a cell, is typically carried out by detecting a particular component, such as a cell-surface molecule, and that both the component and the bacteria as a whole can be described as the analyte.

As used herein a "peptide analyte binding molecule" or "ligand" broadly encompasses any peptide reagent that highly preferentially binds to an analyte or target of interest, relative to other analytes potentially present in a sample. A target (analyte) and target-specific (analyte-specific) reagent are members of a binding pair, and either member of the pair can be used as the target-specific reagent in order to selectively bind to the other member of the pair. Examples of target and target-specific reagent pairs include, but are not limited to, antigen and antigen-specific antibody; hormone and hormone receptor; hapten and anti-hapten; biotin and avidin or streptavidin; enzyme and enzyme cofactor; and lectin and specific carbohydrate. The present invention employs peptide analyte binding molecules that are fixed to the nanopipette by chemical linkages, as described below.

The terms "polypeptide", "peptide" and "protein" are used interchangeably to refer to an oligomer or polymer of amino acid residues. The terms apply to amino acid polymers in which one or more amino acid residue is an artificial chemical analogue of a corresponding naturally occurring amino acid, as well as to naturally occurring amino acid polymers.

The term "antibody" refers, as is customary in the art, to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

The terms variable light chain (VL) and variable heavy chain (VH) refer to these light and heavy chains respectively.

The term antibody as used herein includes antibody mimics and antibody fragments. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH:VL heterodimer which may be expressed from a nucleic acid including VH- and VL-encoding sequences either joined directly or joined by a peptide-encoding linker. Huston, et al. (1988) *Proc. Nat. Acad. Sci. USA,* 85:5879-5883. A number of structures for converting the naturally aggregated but chemically separated light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405 and 4,956,778.

The term "antibody polypeptide" means a polypeptide having immunological specificity to discriminate between different epitopes and bind with high affinity to the cognate antigen, typically with a Kd=about $1 \times 10^{-8}$ M, or between $10^{-4}$ M and $10^{-11}$ M. Such polypeptides may include the above referenced IgG antibodies and antibody fragments, as well as specific binding peptides such as high affinity receptors, or other peptides obtained e.g., by screening a phage display library for binding specifically to an analyte of interest, as is known in the art (See, e.g., U.S. Pat. No. 6,828,110, to Lee, et al., issued Dec. 7, 2004, entitled "Assays for detection of *Bacillus anthracis*," describing polypeptides that specifically bind to *B. anthracis*.)

The term "current detecting circuit" may comprise any sensitive device for detecting changes in current on the order of 1-10 picoamperes, based on a baseline current of 10-1000 picoamperes. The term further refers to a circuit that is time responsive and relatively temperature independent or allow for changes in temperature to be compensated for. It should have an input in a circuit where a known voltage is supplied. Sensitive detecting circuits are known, including voltage clamp amplifiers and transimpedance amplifiers. The term "voltage clamp" here refers to circuits which utilize a differential amplifier having one input connected to a variable command voltage, another input connected to a measured voltage, and a feedback circuit. The voltage clamp uses negative feedback to maintain the system at the command voltage, which in this case is a predetermined alternating signal, such as an alternating voltage signal from a signal generator. The output current follows changes in the input voltage and small changes in current can be detected.

The term "quartz" is used herein as a nanopipette media is a fused silica or amorphous quartz, which is less expensive than crystalline quartz. Crystalline quartz may, however, be utilized. Ceramics and glass ceramics and borosilicate glasses may also be utilized but accuracy is not as good as quartz. The term "quartz" is intended and defined to encompass that special material as well as applicable ceramics, glass ceramics or borosilicate glasses. It should be noted that various types of glass or quartz may be used in the present nanopipette fabrication. A primary consideration is the ability of the material to be drawn to a narrow diameter opening.

The term "electrolyte" is used herein to refer to a material that contains electrolyte solids, i.e., free ions. Typical ions include sodium, potassium, calcium, magnesium, chloride, phosphate and bicarbonate. Other ionic species may be used. The material will typically be liquid, in that it will comprise the sample, containing the analyte, and the ions in solution. The sample itself may be an electrolyte, such as human plasma or other body fluids, water samples and so on. The electrolyte should carry an ionic current; about 10-100 mM, preferably about 100 mM of positive and negative ionic species are thought to be required for this function. The present device may employ either the same or different electrolytes in the nanopipette interior and in the sample material.

The term "protein A" refers to a 40-60 kDa MSCRAMM surface protein originally found in the cell wall of the bacteria Staphylococcus aureus. It is encoded by the spa gene and its regulation is controlled by DNA topology, cellular osmolarity, and a two-component system called ArlS-ArlR. It has found use in biochemical research because of its ability to bind immunoglobulins. It binds proteins from many of mammalian species, most notably IgG's. It binds with the Fc region of immunoglobulins through interaction with the heavy chain. In certain aspects, the present methods use a protein comprising protein A, meaning a fusion protein, but also including other protein constructs which have a high binding capacity for the Fc portion of immunoglobins. Further exemplary details may be found in EP0324867, "Fc-binding protein and strain of producing the same."

Generalized Method and Apparatus

Using finely drawn capillary like tubes, functionalized by chemical linkage to antibodies or peptide-based antibody-like molecules, target antigens are detected. The target antigens may be protein molecules which are introduced into the nanopipette and pass a specific binding molecule attached to the nanopipette tip. If they bind permanently, a permanent blockage of the ionic current is detected. The permanent blockage event is positive identification of the target molecule. In this detection system, target protein molecules in a sample can be uniquely identified by relatively permanent binding (long lasting) to the specific probe molecule attached to the nanopipette tip.

The primary target molecules used in the examples below were two cancer biomarkers, VEGF and IL-10. Biomarkers are indicators of change in protein expression related to disease and the progression of disease. Therefore they are commonly used for clinical diagnosis and analysis of the disease's stage. In addition, biomarkers help in the tailoring of treatments for diagnosed individuals. However, the biomedical techniques used for protein analysis today are not well developed and a new tool is needed for rapid, multiplexed and accurate analysis of biomarkers.

Two different cancer biomarkers were used in this project; Vascular Endothelial Growth Factor (VEGF) and interleukin-10 (IL-10). VEGF is a growth factor protein inducing increased endothelial cell permeability, angiogenesis, and endothelial cell growth, thus promoting metastasis. Occurrence of over expression of VEGF has been found in many types of cancers, for instance breast cancer and colorectal cancer, and is correlated with poor prognosis of survival in these cancer patients. IL-10 is an immunosuppressive and anti-inflammatory agent produced within the body, and it is also known as "human cytokine synthesis inhibitory factor"

because it suppresses the production of cytokines. The correlation between cancer and IL-10 is somewhat ambiguous since it can both serve as a growth factor for cancer cells and promote the innate immune effector mechanisms leading to cancer cell destruction. Even though IL-10 over expression cannot be correlated to cancer patient survival prognosis, it is highly related to cancer and for this reason it can be used as a biomarker in cancer diagnosis. Other antigen-antibody combinations may be used; any specific protein-ligand interaction may provide appropriate molecules for use in the present methods and devices. The present examples enable the development of multiplexed nanopipette technology into a diagnostic device with the ability of real-time protein detection in complex samples, with greater sensitivity and specificity than existing techniques such as ELISA and surface plasmon resonance sensors. A multiplexed nanopipette biosensor should be able to make detections within small human sample volumes and at low target concentrations.

Once the surface chemistry proof-of-principle was established, the resultant surface chemistry was implemented on the nanopipettes. Voltage clamp type measurements were performed with functionalized nanopipettes as bio sensors with the goal of proof-of-principle. Sensitivity, selectivity, and robustness of the nanopipette platform were investigated involving two different cancer marker proteins.

As shown in FIG. 1, the present apparatus comprises functionalized nanopipettes having inserted therein electrodes and arranged to contact an analyte solution 118 and detection circuitry. In this case, two amplifiers 102, 104 are used for detection of current blockage at the tip of the nanopipettes, because two nanopipette electrodes are used. The two working electrodes 114 are separated by an electrolyte gel 126 exemplified below by agar. Two circuits are used, applying voltages V_ch1 and V_ch2, one voltage supply to each pipette. The applied voltage to each of the nanopipettes result in currents I_ch1 and I_ch2, separate current responses at the tips of the nanopipettes. The A/D converter 110 converts the analog voltage signal to numbers for data analysis and presentation.

One benefit from the present nanopipette-based biosensors is that they provide an electrical-based detection method, and thus a simpler and faster system; the assay involves no gels, fluorescent or radioactive labels, dyes or beads. This makes nanopipette biosensors an easy to use, sensitive and cost efficient tool in diagnostics. In addition, nanopipette fabrication is a single-step relatively cheap process and the fabricated nanopipettes are easy to tailor to different types of experiments and applications. Immunoanalytical methods are adaptable since we can produce antibodies against almost any particular compound.

The electrolyte gel acts as a filter to allow electrolyte and thus ionic current to pass through the materials (i.e., electrolyte ions such as K+, Cl—, etc.), while preventing analyte (e.g., IL-10) molecules from passing between the two electrode containing materials. Changes in analyte in the bath having the working electrode will not affect the reference electrode. Other filter materials besides agar can be used. These include actual membrane materials or other gel materials, such as polyacrylamide or agarose gels. The electrolyte gel filter serves to minimize cross contamination when two different analytes are being measured, that is, if nanopipettes 113a, b are functionalized with two different ligands to detect two different analytes in a single sample. A high degree of multiplexing is possible with the present device; for example, a positive control pipette with a ligand to a known analyte, a negative control pipette, with a ligand to an absent analyte, and ten different sample-testing nanopipettes could be clustered in a single support, owing to the small size of the pipettes. Another advantage of using an electrolyte permeable gel is that the reference electrode 116 does not see analyte and may be reused easily in different tests.

As As shown in FIG. 2A-C, antibodies (or other peptide ligands) are attached in the vicinity of the tip of the nanopipette 204. The tip vicinity may be regarded as being within the ring of the opening, or on the inside or even the outside, within a distance of several molecular diameters of the analyte to be detected. Antibodies may be attached to the outside of the nanopipette as well as the inside, as long as there are a number of antibodies near the tip. Antibodies should not be attached beyond 1 mm from the tip opening, preferably not beyond 0.5 mm of the tip opening. The antibodies are attached by direct chemical linkage to the glass or quartz surface. The antibody at the tip will bind to an antigen, causing a detectible current blockage, provided that the right detection circuit is used. As shown at FIG. 2A (first step), protein molecules 206 will be contained in or extracted from the sample to be tested. The specific binding molecules 202 will be attached to the nanopipette tip (second step; FIG. 2B). Chemistry for tightly binding the antibodies to the tip region is described below. FIG. 2C illustrates the mechanism whereby a passing molecule 208 specific for the binding molecule will be detected upon its passage through the channel in the nanopipette (third step).

Figure 3:
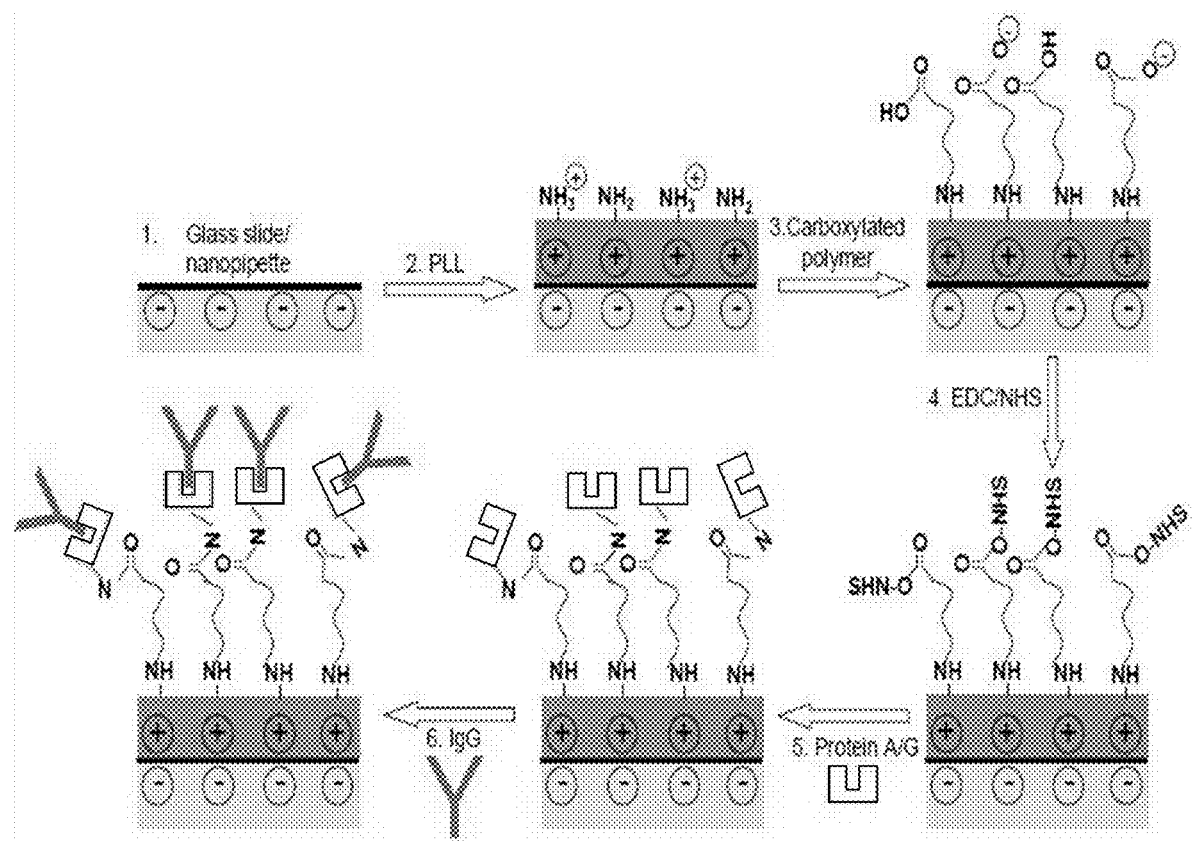
FIG. 3 is a schematic diagram showing chemical functionalization of a glass surface, such as nanopipette tip, for attachment of peptide ligands.
Figure 4A:
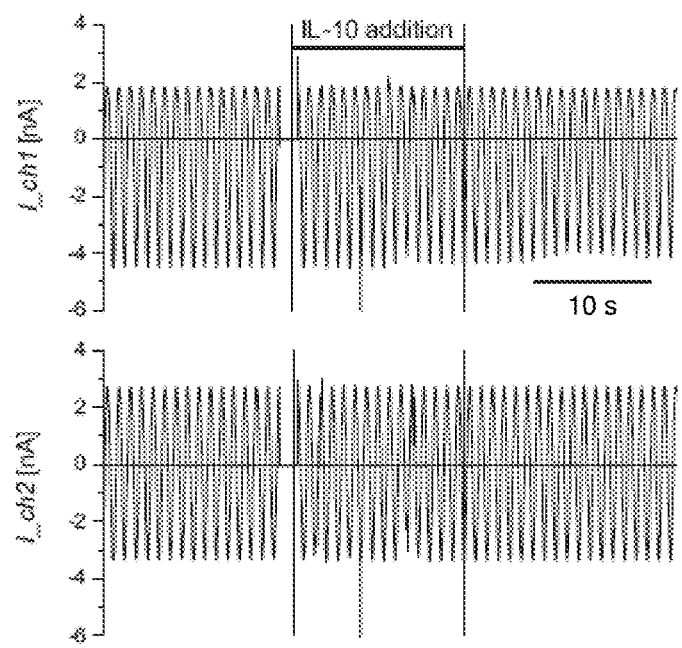
FIG. 4A and 4B is a set of graphs showing current traces from addition of IL 10 (FIG. 4A) and VEGF (FIG. 4B) to the device as illustrated in FIG. 1. The line data as presented in the following
Figure 4B:
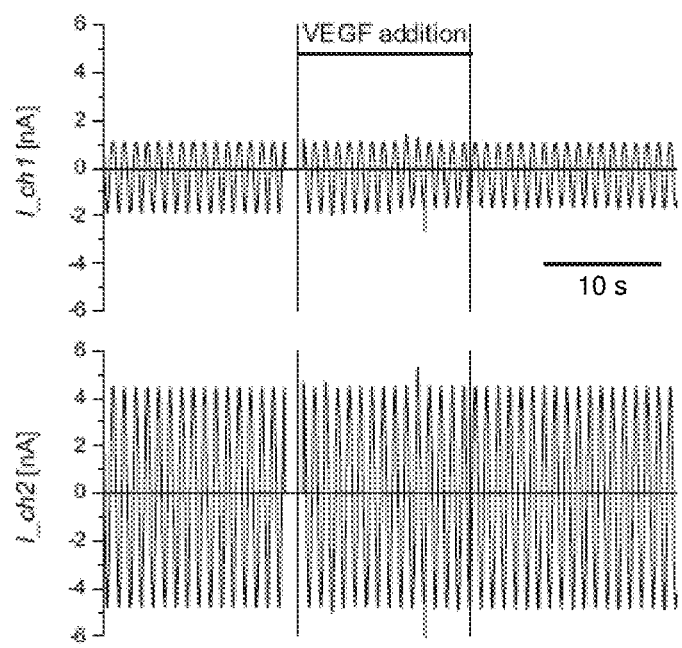

FIG. 3 shows a series of six steps in which a glass or quartz nanopipette is chemically modified for covalent linkage of antibody proteins (or other peptide binding molecules) to the surface. In step 1, the negatively charged glass slide/nanopipette (1.) is coated with a monolayer of poly-l-lysine (PLL) (2.) altering the charge and supplying amine groups. Next, the surface is treated with a carboxylated polymer such as polyacrylic acid or polymethacrylic acid, containing multiple carboxyl groups (3.) and with the help of the crosslinker EDC/NHS (4.), (1-Ethyl-3-(3-dimethylaminopropyl)-carbodiimide/N-Hydroxysuccinimide) a linkage between the surface and added Protein A/G (5.) is formed. As described in detail below, the EDC/NHS has been previously used in other contexts to provide an amide bond. In the final step, antibodies are immobilized (6.) onto the glass slide surface. The underlying surface chemistry was developed with glass slide experiments, was subsequently implemented to the nanopipettes and is shown in FIG. 3. To enable protein immobilization onto the glass pipette, there is a need to change its negatively charged properties since most proteins have a net negative charge. Numerous protocols had to be investigated in order to establish what protocol would be implemented to the nanopipette biosensors. Direct covalent coupling of the ligand peptide is preferred. This can be done by NHS linkage, silanization, or the method described above, which involves coating the glass with a PLL layer, a carboxyl layer, and then using EDC/NHS coupling. It is also desirable to couple the antibodies through a protein that binds to the Fc portion of the antibody, such as protein A/G, as described below. Protein A/G is a genetically engineered protein that combines the IgG binding profiles of both Protein A and Protein G. Protein A/G is a gene fusion product secreted from a non-pathogenic form of *Bacillus*. This genetically engineered Protein A/G is designed to contain four Fc binding domains from Protein A and two from Protein G. Silanization may be used to couple the peptide binding molecule to the nanopipette tip as described, e.g. in U.S. Pat. No. 5,077,210, issued Dec. 31, 1991. Various methods for coating inorganic substrates with silane films have been reviewed, Weetal H. H. (1976) Methods in Enzymology, Volume 44, 134-148, Academic Press, New York, N.Y. Inorganic porous substrates coated with epoxy silane have been oxidized to produce aldehyde groups reacting directly with antibodies, Sportsman, J. R. et al (1980) Anal. Chem. 52,2013-2018. Others, such as Sagiv U.S. Pat. No. 4,539, 061, have established multilayers of silanes deposited on silica. Proteins have further been linked to silane films on silica using glutaraldehyde. See U.S. Pat. No. 4,478,946, Mandenius, C. F., et al (1984) Anal. Biochem. 137, 106-114, and Richards, F. M. et al (1968) J. Mol. Biol. 37, 231-233. Reactive crosslinkers such as glutaraldehyde may bind to many residues and form multi protein complexes which could interfere with protein function. To avoid the use of glutaraldehyde, others have modified silica surfaces with epoxy silanes and subsequently altered the silanes to have a dihydroxy terminus, U.S. Pat. No. 4,562,157.

Protein A/G binds to all human IgG subclasses. In addition, it binds to IgA, IgE, IgM and to IgD but to a lesser extent to IgD. Thus, Protein A/G may be a preferred ligand in tests for or tests using non-IgG class immunoglobulins.

The basic surface chemistry used in the glass slide proof-of-principle and the nanopipettes has the following steps: First the slide is coated with poly-L-lysine (PLL) solution and then baked. The polycationic property of the PLL molecule allows it to bind electrostatically to the negative quartz surface and gives the surface a better ability to bind to proteins by its amine groups. Secondly a carboxylated polymer is applied. The carboxylated polymer, which is poly acrylic acid, becomes a carboxyl acid in aqueous solution and overcoats the PLL, thus canceling the positive charge. 1-Ethyl-3-[3-dimethylaminopropyl]carbodiimide hydrochloride/hydroxysulfosuccinimide/N-hydroxysuccinimide (EDC/NHS) is used as a coupling agent for applied proteins. The EDC/NHS system is described in the literature, e.g., in J. S. Daniels and N. Pourmand, "Label-free impedance biosensors: Opportunities and challenges," *Electroanalysis*, vol. 19, no. 12, p. 1239, 2007. 1-Ethyl-3-[3-dimethylaminopropyl] carbodiimide hydrochloride (EDC or EDAC) is a zero-length crosslinking agent used to couple carboxyl groups to primary amines. This crosslinker has been used in diverse applications such as forming amide bonds in peptide synthesis, attaching haptens to carrier proteins to form immunogens, labeling nucleic acids through 5' phosphate groups and creating amine-reactive NHS-esters of biomolecules. EDC reacts with a carboxyl to form an amine-reactive O-acylisourea intermediate. If this intermediate does not encounter an amine, it will hydrolyze and regenerate the carboxyl group. In the presence of N-hydroxysulfosuccinimide (Sulfo-NHS), EDC can be used to convert carboxyl groups to amine-reactive Sulfo-NHS esters. This is accomplished by mixing the EDC with a carboxyl containing molecule and adding Sulfo-NHS.

Thus, EDC is used here to couple carboxyl groups with proteins' amine groups. When EDC reacts with a carboxyl it creates an amine-reactive intermediate. If an amine bond is not created the intermediate is hydrolyzed and the carboxyl group is regenerated. In the presence of NHS, the EDC intermediate is stabilized by the formation of a NHS ester and thereby NHS increases the efficiency of EDC. In order to minimize non-specific binding, BSA was used as a blocking agent. The slide was scanned at 532 nm and the fluorescein dyed streptavidin bound to the immobilized biotinylated antibodies was visualized. Non-biotinylated anti-ferritin IgG was used as negative control.

Immobilization protocols including biotinylated and Cy3 conjugated oligocleotides and biotinylated BSA as probe molecules were tested, but proved to be less successful and were therefore not further pursued experimentally.

After adding a coupling layer of NHS esters, Protein A/G was added. Protein A/G is a genetically engineered, highly specific protein that binds to the Fc-region of IgA or IgG. Protein A/G is commercially available, e.g., from Pierce Protein Research Products. Protein A/G is a genetically-engineered protein that combines the IgG binding domains of both Protein A and Protein G. It is a gene fusion product expressed in *E. coli*. Protein A/G contains four Fc binding domains from Protein A and two from Protein G, resulting in a final mass of 50,460 daltons (40-45 kDa by SDS-PAGE). Protein A/G is not as pH dependent as Protein A, but otherwise has the additive properties of Protein A and G. Protein A/G was utilized since it gives the surface the preferred alignment of the antibodies, e.g., active sites will be available to antigen binding, thus enhancing the effectiveness of the surface. After incubation over night in cold room with protein A/G the surface is ready for antibody immobilization.

Figure 5:
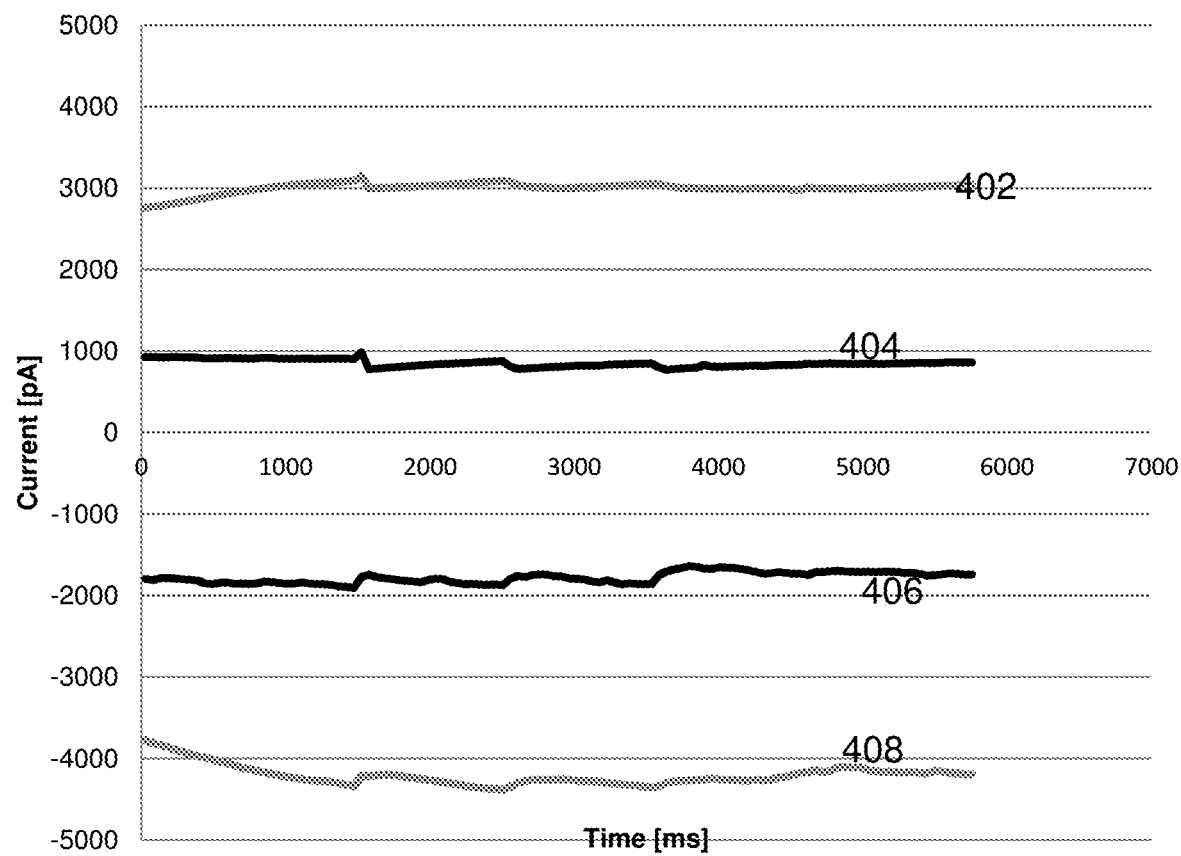
FIGS. 5-8 are simplified in that only the peaks are shown; the peaks are connected to present a single line representing a connected series of dots from the peaks.

The target molecules passing through the nanopipette tip create characteristic blockage events of the ionic current. FIG. 5 shows results from the addition of a detected analyte (IL-10), lines 404 and 406, and a control analyte, ferritin, lines 402 and 408 (top and bottom lines).

Figure 6:
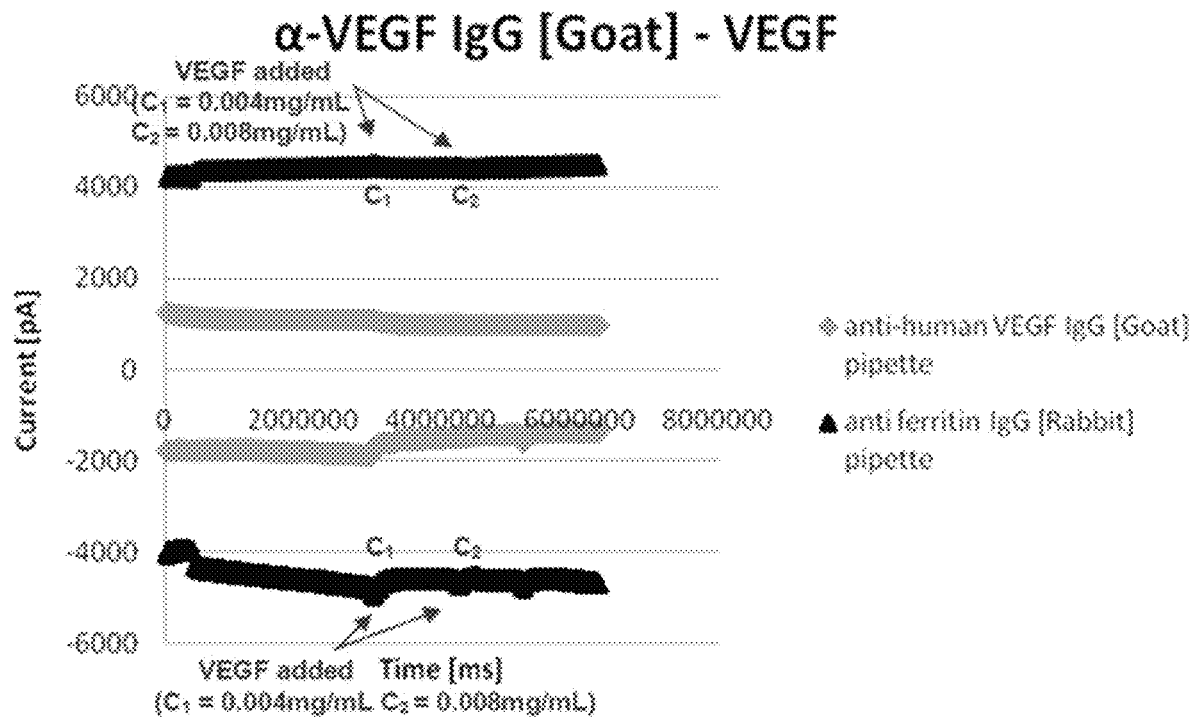
Figure 7:
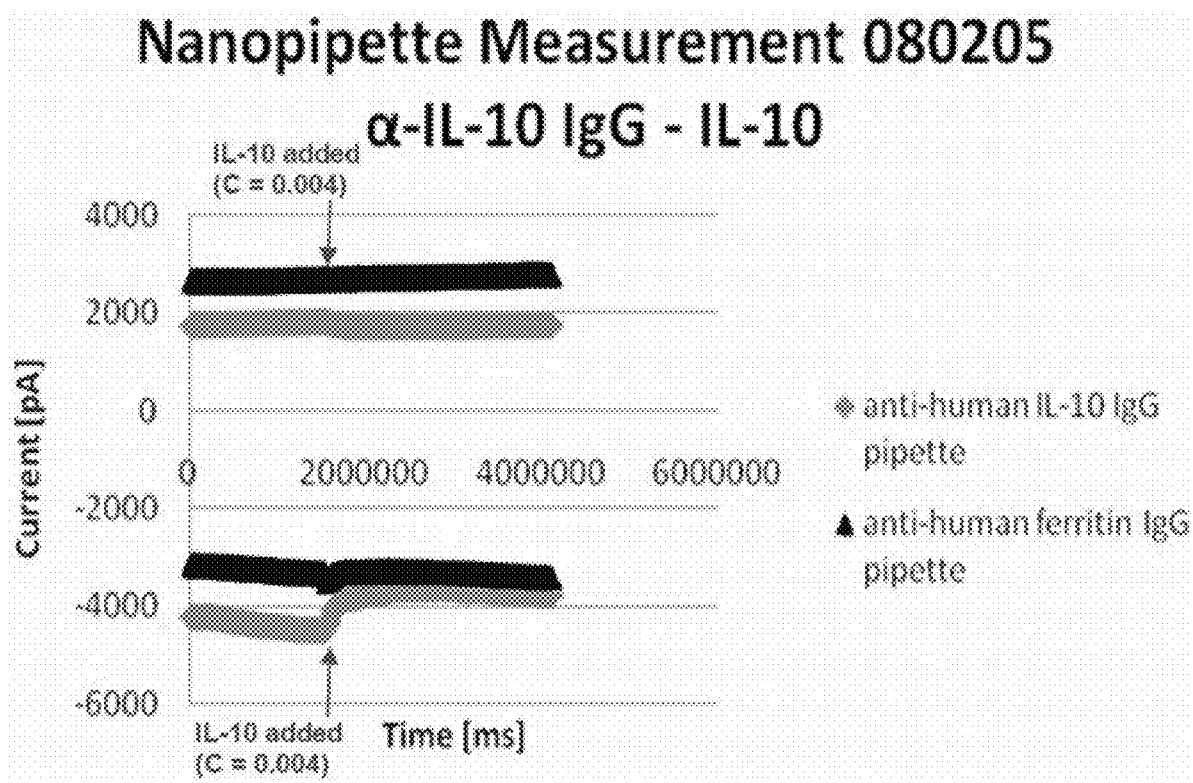

Other experiments (FIGS. 6-8) further demonstrated experimentally the detection of antigen-antibody interactions.

An important aspect of the present invention is the circuitry that is applied to the functionalized nanopipettes. Electrodes are placed in the nanopipette and in an external electrolyte solution. One external electrode is a reference electrode. An alternating voltage is applied to the working electrode(s). This produces positive and negative ionic currents. Both are detected. A relatively low frequency alternating voltage is used. Computer data processing is used to measure a series of positive and negative current peaks and construct plots of these peaks, such as the lines shown in e.g., FIG. 5, 402-408. Thus, small changes in current flow can be detected and their significance as representing specific molecular interaction at the nanopipette tip can be determined.

The present methods rely on specific protein interactions between the ligands at the tip and the analyte. Exemplified are antibody-antigen interactions. In certain embodiments, one may immobilize peptide antigens on the pipette tip and detect antibody analytes. Different antibodies may be used, and will have differing avidity and affinity for their cognate antigens. In addition, different pipette tips will contain different numbers of immobilized antibodies in the tip region, due to manufacturing variations. To this end, target molecules in a sample can be further uniquely identified by statistical or pattern recognition signal analysis of blockage events while passing through the nanopipette tip. It is not necessary to rely on labeling the antigen to be detected in the present methods. The analysis system will include the ability to take a clinical sample and test for the presence of specific molecules. In general, the task is to distinguish between various molecules passing through the nanopipette and creating characteristic blockage events.

EXAMPLES

Example 1

Nanopipette Fabrication

Fabrication of "nanochannels" in glass capillaries results in what is referred to as a "nanopipette." Nanopipettes are fabricated using thin-walled quartz capillaries with, for example, an initial inner diameter of 0.7 mm. Different inner and outer capillary diameter can be used to achieve variations of shapes and sizes of nanopipettes. These pipettes are placed into a laser-based pipette puller (e.g., as available from Sutter instruments, Novato, Calif.), and the resulting "needle" can have a channel with smallest outer diameter of 10 nm at the tip (according to Sutter Instruments puller manual). Stanford has produced nanopipettes with outer diameter of approximately 50 nm at the tip, with the smallest observed outer diameter of 37 nm. The range of tested pipette outer diameters has been 37-82 nm, with an average of 56 nm. The tip opening would be on this order of size. Although the preferred material is quartz, other materials may be used. A variety of materials consisting primarily of silicon dioxide are known and may be obtained commercially, e.g., from Technical Glass Products, Inc., Painesville Twp., Ohio.

Ionic current consistent with the observed dimensions can be seen when the fabricated nanopipettes are filled with KCl solution. For example, with 100 mM KCl solution, the current measured in one pipette tip was approximately 200 pA with an applied voltage of 50 mV. This is consistent with an inner tip diameter of approximately 40 nm (Equation 1). Furthermore, the linear relationship between voltage and observed current indicates that the nanochannel is not selective for the ions in the solution and that there is no effective ionic gradient. This also suggests that the nanochannel resistivity for this solution is directly related to the nanochannel dimensions.

The pipette tip geometry and corresponding resistance has been described (Sakmann & Neher, 1995, Ch. 21). In general, the resistance of the pipette is the sum of elementary resistances represented by slabs of fluid with area A(x) and length dx:

$$R = \int_{x1}^{x2} \frac{\rho}{A(x)} dx \qquad [1]$$

The nanopipettes have been fabricated, and ionic current through these nanopipettes has been observed. Furthermore, blockages of current due to nanoparticles flowing through the pipette were also observed, with results shown below.

The shape of the nanopipette is conical up to the close proximity of the tip. The very end of the tip (approximately the last 500 nm in length) has a conical angle that appears to be much steeper in cone angle at the end of the tip. The tip having a 52.2 nm opening was observed to have about a 100 nm radius of curvature at the tip.

A nanopipette tip may be examined by a scanning electron microscope for appropriate geometry. Typically, it will have an elongated frusto-conical "base" or "top," tapering down into a narrower, finely drawn tip, ending in a sharp tip, nearly pointed, with a small opening (e.g., ~50 nm) at the end.

The nanopipette tip is approximately conical. A feature of the conically shaped nanopipette is that current change is focused to an area just inside of the nanopipette tip, thus creating a 'sensing zone' (See, Lee, S., et al., Electrophoretic capture and detection of nanoparticles at the opening of a membrane pore using scanning electrochemical microscopy. *Anal Chem*, 2004. 76(20): p. 6108-15.

The total resistance of the pipette is given by the sum of the cylindrical shank resistance and the resistance for the conical tip (Equation 2.1). (See, Sakmann, B. and Neher, E. *Single Channel Recording,* Second Edition Chapter 21, pgs 638-639. Plenum Press, New York, 1995.) The resistance of the tip dominates since the radius of the shank, $r_s$, is a lot bigger than the radius of the tip, $r_t$.

Equation 2.1 shows total resistance, R, of a nanopipette. $\rho$ is the electrolyte resistivity, l is the length of the nanopore and $\theta$ is the angle of the nanopipette tip cone.

$$R = \frac{\rho l}{\pi \cdot r_S^2} + \frac{\rho \cot(\theta/2)}{\pi}\left(\frac{1}{r_t} - \frac{1}{r_S}\right) \qquad 2.1$$

This focused effect results in a very good detection system that is extremely sensitive to analyte molecules in the electrolyte, a phenomenon not seen in cylindrical nanopores.

In the present work, nanopipettes were fabricated from quartz capillaries with filaments and with an outer diameter of 1.0 mm and an inner diameter of 0.70 mm (Sutter Instruments, Novato, Calif., USA). The capillary was placed in a P-2000 laser pipette puller machine (Sutter Instruments, Novato, Calif., USA) pre-programmed to fabricate nanopipettes with the inner diameter of ~50 nm. Parameters used were: Heat=700, Fil=4, Vel=60, Del=150 and Pul=192 and alterations of these parameters can change the scale of the fabricated nanopipette tip. With the pre-set parameters mentioned nanopipettes tips with inner diameters ranging from 37 to 82 nm have been produced and tested with the mean size being 56 nm (See, Karhanek, M., et al., "Single DNA molecule detection using nanopipettes and nanoparticles," *Nano Lett*, 2005. 5(2): p. 403-7.)

Example 2

Measurement Apparatus Setup and Procedure

The present apparatus is exemplified and illustrated in FIG. 1. Quartz glass nanopipettes 113 were fabricated and filled as described above with antigen solution 118. The antigen is in the nanopipette and the electrolyte/analyte solution 120 into which the nanopipette is inserted. The antigen may be in a mixed and dilute form, and it will be specifically identified from a complex mixture. Nanopipettes 113a, b are placed into a pipette holder (Axon Instruments, or Warner Instruments Corporation, Hamden, Conn.). The pipette holder is then attached to a MM-33 micromanipulator (Sutter Instruments Company) (not shown). Each nanopipette 113a, b contains an electrode 114a, b that is connected individually to an Axopatch 200B amplifier (Axon Instruments, Foster City, Calif.). Each electrode 114 is connected to a headstage 106, 108. This serves to reduce noise; the circuitry is also shielded in a faraday cage. Each headstage 106, 108 (Axopatch 200B and CV 203BU) was input to an operational amplifier at a negative input, where the positive input is grounded or connected to a command voltage. The command voltage may be set at different levels as is known in the field of voltage clamp circuitry. The amplifiers are output to an analog to digital converter for data interpretation and storage by a computer. A digital to analog converter connected to a computer is used to provide the command voltages.

The sample solution 120, consisting of 10-100 mM KCl, is placed into a small beaker or on a hydrophobic surface resulting in a large drop of approximately 150 microliters. The pipette tips containing antibodies 130, 132 are then carefully immersed into the solution and the test antigens are added to the solution next to the immersed pipette tip or inside of the pipette.

Ionic current is recorded using the Axopatch 200B amplifier in voltage-clamp mode with signal filtering at 5-10 kHz bandwidth. Holding Command to set voltage commands in voltage clamp and current commands in current clamp, one makes a choice of three gain settings on the dedicated current output based on nanopipette and working solution conditions.

The signal is further digitized by an Axon Digidata 1320A digitizer with sampling frequencies from 10 kHz to 500 kHz. The data is recorded using Clampex 8 (Axon Instruments), and the same software is used for basic signal analysis.

The nanopipette biosensor technology is based on an electrochemical cell consisting of an electrolyte (working buffer; 100 mM KCl, 2 mM Phosphate) and two Ag/AgCl electrodes; one working electrode inserted to the electrolyte filled nanopipette and one reference electrode 116. The working electrode and the reference electrode are in separate baths connected through electrolyte solution in an agar gel filled box. The agar gel 126 keeps the baths separated and prevents analyte contamination. When voltage is applied to the circuit, ions will flow through the nanopipette opening, creating a steady current flux. This ionic current is modified by changes in the nanopipette tip region and may be blocked, partially or fully, by molecules translocating the opening. Nanopipette detection can be readily adapted for multiplex protein detection by using several nanopipettes, each with a different immobilized probe protein, immersed in the same electrolyte bath. After applying voltage to the system and upon addition of target protein to the nanopipette bath, the nanopipette with the complementary probe protein immobilized on its surface will differentiate itself against other nanopipettes through a unique change in its current profile. This way the target protein or other antigen can be identified.

Apparatus Comprising Electrode Baths Separated by Electrolyte Containing Filter Material Making the Agar Gel Box 200 mL buffer (100 mM KCl, 2 mM Phosphate) was microwaved together with 2 g of agar powder until all the powder had dissolved. Then about 50 mL agar liquid was poured into an empty and clean pipette box and was put in cold room to stiffen. Agar gel filled plastic pipettes were also made by pipetting hot aqueous agar gel up into the pipettes and then left to harden. Working buffer was poured onto the gel in the gel box, and the level of agar gel and buffer solution was marked.

Voltage Clamp Measurements

A voltage clamp device controls, or clamps, a nanopore potential at any level decided by the researcher. The voltage clamp technique was here used to investigate how applied potential affects the ionic current flow through the nanopipette, and how changes in the nanopipette tip region and in the nanopipette surface influence this ionic current.

The electric potential in the nanopipette tip is affected by the surface charge of the nanopipette. In the presence of a surface charge, an electric double layer (EDL) of counter ions is recognized to be formed at the surface/electrolyte interface and causes the nanopipette to become ion permselective (See, FIG. 9 and Wei, C., A. J. Bard, and S. W. Feldberg, Current rectification at quartz nanopipette electrodes. *Analytical Chemistry*, 1997. 69(22): p. 4627).

A quartz nanopipette without any modifications has a negative surface charge; hence an EDL containing $K^+$ ions will be formed with a KCl electrolyte solution. This phenomenon is reduced by higher electrolyte concentrations but a 100 mM KCl electrolyte concentration, as used in this project, gives rise to an EDL of about 1 nm, according to Wei et al.

There are two analyte detection principles with nanopipette biosensors; analyte or nanoparticle blockage of ion current leading to temporal reduction of ion current explained by Karhanek, et al., and change in nanopipette surface ion conductivity induced by binding events. The experiments in the scope of this project made use of the latter detection method.

The functionalized pipettes were filled with working buffer (100 mM KCl, 2 mM Phosphate, pH=7.0, σ=12.1 [mS/cm]. Filling was performed first through capillary forces by putting the shank side of the nanopipette into 40 μL buffer and visually seeing the tip being filled. Then the shank of the nanopipette was filled with working buffer with the help of a syringe pipette. Finally the filled nanopipettes were mounted in the pipette holder (Axon Instruments Inc., Foster City, Calif., USA). Ag/AgCl working electrodes and a reference electrode were fabricated with silver wire and Clorox bleach and the working electrodes were attached to the nanopipettes in the pipette holder. The nanopipettes and the reference electrode were immersed into electrolyte baths in a 1% agar gel box. As shown in FIG. 1, a reference electrode 116 was placed in an electrolyte solution 122 which is physically separated from the pipette solution. It is separated by an electrolyte gel 126. Electrolyte solution is also contained in a bath into which two nanopipettes are inserted so that the tip openings are submerged. Each of the two pipettes contains a working electrode 114. In addition, a nanopipette may be provided with a working electrode which is not functionalized with the antibody type molecule of interest, to serve as a negative control. Each nanopipette has a port for addition of electrolyte and, optionally, analyte. The working electrodes 114, 114a may have a different antibody 130, 132 immobilized in the vicinity of the tip. One antibody may be selected to give no binding to materials in the sample, and serve as a negative control. Alternatively, a nanopipette may be provided with an antibody to a known marker added to the sample, providing a positive control. While only two electrodes/nanopipettes are illustrated in FIG. 1, it is understood that numerous functionalized nanopipettes may be simultaneously inserted into the sample.

Each working electrode 114 was connected to an Axopatch amplifier applying input voltage and measuring output current. The analog signal was low-pass filtered at 50 kHz with a four-pole Bessel filter. The amplified, filtered signal was digitized at 250 kHz with a NI PCI-6014 DAQ card (National Instruments, Austin, Tex.). Data acquisition was controlled with custom software written in LabWindows/CVI (National Instruments). Data analysis was implemented in MatLab (The MathWorks, Natick, Mass.). The Axopatch output is connected to the A/D converter that is in turn connected to a computer with Clampfit data analysis program. A voltage cosine wave, +/−200 mV, was applied to the circuit and current response was measured. It can be seen in FIG. 1, that a digital to analog converter 112 is connected to the input(s) (positive in this example) of an amplifier such as shown at 103 and acts as a signal generator to provide a predetermined alternating voltage. Head stage amplifiers 106, 108 are connected between the electrodes and the amplifier 102 input. These are shielded to prevent noise, as by a Faraday cage. As described below, current changes being measured are on the order of 3-20 picoamperes, and sensitive detection circuitry is needed. Different analytes were added to the working electrolyte bath and current change was subsequently analyzed. The cosine wave could alternatively be a sine wave. It is important to use a voltage which alternates, so that rates of current change in different polarities can be measured. A square wave or other shape could be used with proper corrections. The frequencies employed here have been found to be most favorable in a very low range, around one Hz (e.g. 0.5-10 Hz). The Digital to analog converter 112 is used as a signal generator to the inputs of the amplifier and is computer controlled to enable selection of desired frequencies and amplitudes.

Example 3

Glass Slide Protocol for Determining Protein Binding Conditions

A glass slide may be used for development or modification of a chemistry for attaching a ligand to a nanopipette. In this example, a glass surface is modified with a positive charge whereby a peptide bond may be created with a protein ligand, namely the Fc portion of an antibody, e.g., biotinylated anti-human ferritin IgG. Attachment of the antibody may be demonstrated by capture of fluorescence-coupled streptavidin.

A glass slide (Gold Seal Products, Portsmouth, N.H., USA) was cleaned in a sonicator for 30 minutes at room temperature. The slide was coated in 0.01% poly-L-lysine (Electron Microscopy Sciences, Hatfield, Pa., USA), size 30,000-70,000 kDa, for 5 minutes at room temperature. Subsequently, the glass slide was baked in 120° C. for one hour to evaporate the water bound with the PLL. Next the slide was incubated for 10 min in carboxylated polymer solution at room temperature. After washing the slide in water three times and blow drying it with argon gas it was incubated with EDC/NHS (Pierce Biotechnology, Rockford, Ill., USA)/(Pierce Biotechnology, Rockford, Ill., USA) for one hour at room temperature. EDC 5 weight % and NHS 5 weight % aqueous solution was prepared just before incubation since EDC is unstable in water. After one hour the slide was thoroughly washed with water before it was incubated with 0.1 mg/mL Protein A/G (Pierce Biotechnology, Rockford, Ill., USA) and put in a moist chamber in the cold room over night. The next morning, 0.5 mg/mL of biotinylated anti-human ferritin IgG (Rockland Immunochemicals, Inc., Gilbertsville, Pa., USA) in buffer was spotted onto the glass slide surface and incubated for 30 minutes at room temperature. 0.5 mg/mL of regular anti-human ferritin IgG (Rockland Immunochemicals, Inc., Gilbertsville, Pa., USA) was used as a negative control in this experiment. Three times, the slide was rinsed in 0.1% BSA (Rockland Immunochemicals, Inc., Gilbertsville, Pa., USA) and BSA was then applied to the whole surface and incubated for 30 minutes at room temperature. Fluorescein conjugated streptavidin (Pierce Biotechnology, Rockford, Ill., USA) was added so that it covered the glass slide and it was incubated for 30 minutes at room temperature. The slide was scanned at 532 nm (green light) in a GenePix Pro 6.0, 4000A Microarray Scanner (Axon Instruments Inc., Foster City, Calif., USA).

Example 4

Functionalization of Nanopipettes

After pulling, the nanopipette tips were treated with PLL for five minutes and then baked in the oven in 120° C. for one hour. Nanopipette handling devices, made out of pipette tips and Eppendorf lids, were mounted on a 96-well plate and used for further washings and incubations. Four nanopipettes were mounted in handling devices on a 96 well plate. Nanopipettes were dipped into the carboxylated polymer, polyacrylic acid (from Sigma-Aldrich #323667, average Mw ~1,800) for 10 minutes and then washed with water three times for at least 30 seconds each wash before they were incubated for an hour in EDC/NHS (50 mg/mL EDC, 50 mg/mL NHS). After washing three times in water for at least 30 seconds each wash, the pipettes were put in 0.1 mg/mL Protein A/G solution over night in cold room. Next morning, immobilization of a selected antibody (IgG) took place dipping a nanopipette tip in a 40 µg/ml IgG solution for 1 hr at room temperature to allow the protein A/G to capture the Fc region of the IgG molecule. Anti-human VEGF IgG [Goat] (R&D Systems, Inc., Minneapolis, USA) or anti-human IL-10 IgG [Rat] (BioLegend, San Diego, Calif., USA) were used with a concentration of 0.04 mg/mL. Anti-human ferritin IgG was used as a negative control with the same antibody concentration as for the probe nanopipettes. In preparing the antibody coating, care should be taken to apply antibody primarily to the tip region. No aspiration was used, but tips are held to less than 1 mm insertion into the antibody solution.

Example 5

Antigen and Antibody Interactions

The nanopipette biosensor examples below can be divided into three categories: I) Primary and secondary antibody interaction experiment, II) Antibody-antigen interaction experiment and III) Limit of detection experiment.
I) Primary and Secondary Antibody Interaction Experiment One primary and secondary antibody interaction experiment was performed and anti-human VEGF IgG [Goat] and anti-human ferritin IgG [Rabbit] (control). 10 µL of anti-Goat IgG (Rockland Inc., Gilbertsville, USA) was added twice, with final concentrations of 0.02 mg/mL and 0.04 mg/mL, to the functionalized nanopipette. This approach was not very successful so a different approach was tried. That is, it was found advantageous to have the detection antibodies directly coupled to the glass pipette. This approach did not use chemical coupling of the peptide ligand to the nanopipette tip, and was not found to be optimum.
II) Antibody-Antigen Interaction Experiments Six antibody-antigen interaction experiments were performed.

Two of these were done with an anti-human VEGF IgG [Goat] functionalized nanopipettes adding 10 µL of the antigen, recombinant human VEGF-162 (R&D Systems, Inc., Minneapolis, USA) twice, resulting in concentrations 0.004 mg/mL and 0.008 mg/mL of VEGF in the nanopipette biosensor bath. The VEGF molecule used consists of 162 amino acid residues with a molecular weight of 18.8 kDa, calculated by R&D Systems. Unlike most proteins VEGF has a positive net charge.

Figure 8:
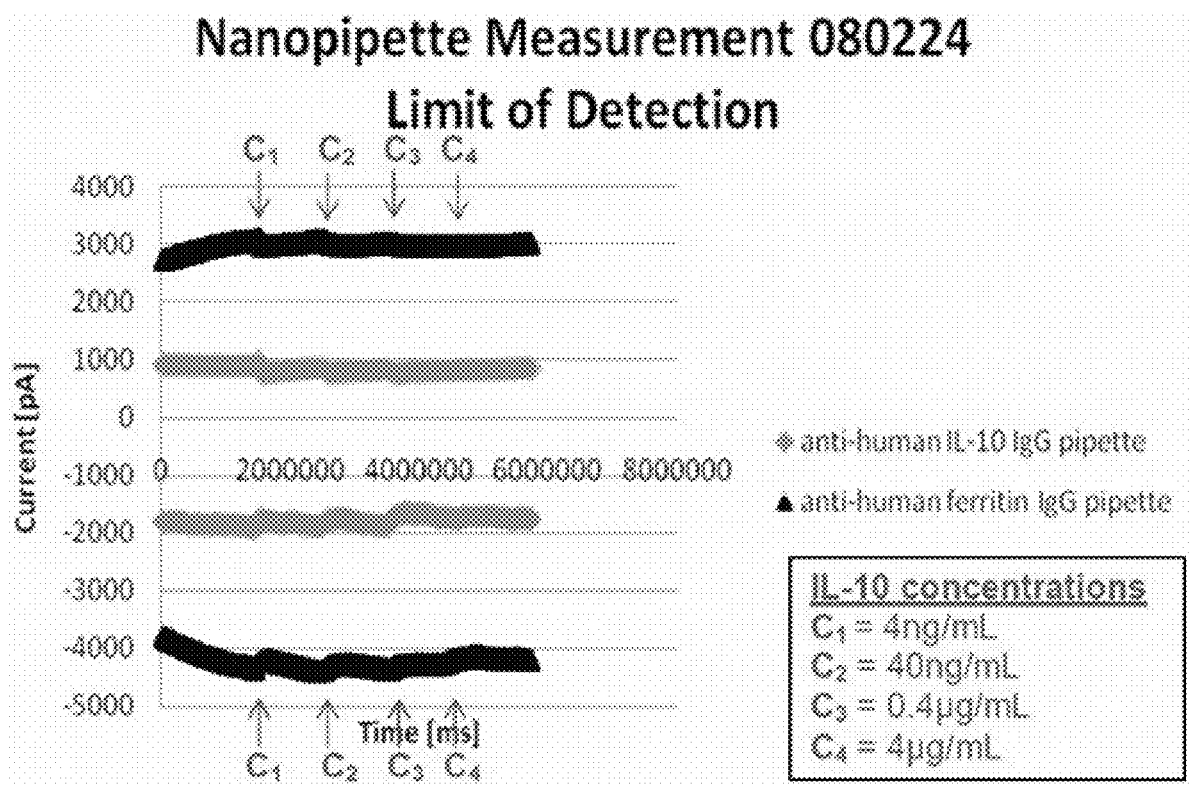

The other four experiments used anti-human IL-10 IgG functionalized nanopipettes. Recombinant human IL-10 (R&D Systems, Inc., Minneapolis, USA), with a molecular weight of 18.6 kDa, was added to the electrolyte solution with the nanopipettes. In these experiments 10 µL of IL-10 solution was added once with a resulting concentration of 0.004 mg/mL. For all the antibody-antigen interaction experiments anti-human ferritin IgG [Rabbit] functionalized nanopipettes were used as a negative control.
III) Limit of Detection Experiment (FIG. 8)

A limit of detection experiment was performed with anti-human IL-10 IgG functionalized nanopipettes adding 10 µL recombinant human IL-10 resulting in four different concentrations, 4 ng/mL 40 ng/mL, 0.4 µg/mL and 4 µg/mL. Also in this experiment an anti-human ferritin IgG [Rabbit] functionalized nanopipette was used as negative control.

Data Analysis

The average current peak values for each sweep, observed on a Molecular Devices Clampfit Screen at ~1 cycle per second, positive as well as negative, were collected on a computer and made into a new peak value graph to enable relative comparison of current changes between the nanopipette functionalized with probe molecules and the negative control nanopipette. The peak current data points were normalized against the baseline upon analyte addition. In this work, a raw data file consisted of multiple sweeps, each sweep being a period, e.g., 50 seconds of measurement of current cycles. During each sweep, 50 cycles of sinusoidal voltage was applied and corresponding peaks in current were measured and averaged. Normalization was done by dividing a given current value by the average immediately before the addition of target molecules for the run. As low as 1% change in current can be detected. Normalization methods are also used to facilitate the differentiation between random noise of various pipettes resulting from different functionalizations. That is, differently prepared pipettes may have different unblocked currents, e.g., between 1500 and 4000 pA. However, current changes resulting from specific binding can still be detected. Values from different pipettes can be normalized to facilitate comparisons of results.

There was no apparent difference between the IgG [Goat] functionalized nanopipette and the IgG [Rabbit] (control) functionalized nanopipette upon addition of anti-goat IgG. Nanopipette measurements in Experiment 071206 (See Table below), examining the measurement of interactions between IgG and anti-IgG Antibody-Antigen Interaction; Anti-Human VEGF IgG [Goat] and Human VEGF Two experiments with anti-human VEGF IgG [Goat] functionalized nanopipettes was carried out. Anti-ferritin IgG [Rabbit] was used for modifying the negative control nanopipette. After adding VEGF twice a change in the negative current profile was seen for the anti-human VEGF IgG [Goat] functionalized nanopipettes in both experiments, indicating specific binding, see FIGS. 4-7.

That the change mainly occurred in the anti-human VEGF IgG nanopipette biosensor was determined. The current response over time was measured after normalization by relative comparison with negative control enabled by normalizing the data. In experiment 080112, a change of 10% in positive current profile and 25% in negative current profile was shown. In the other VEGF experiment the corresponding change was +0/−20%.

Antibody-Antigen Interaction; Anti-Human IL-10 and Human IL-10

Another antibody-antigen pair was tested after VEGF experiments indicated specific binding. Four experiments with anti-human IL-10 IgG functionalized nanopipettes were performed. One experiment showed a small current change and one experiment had no significant current change upon addition of human IL-10.

Figure 9:
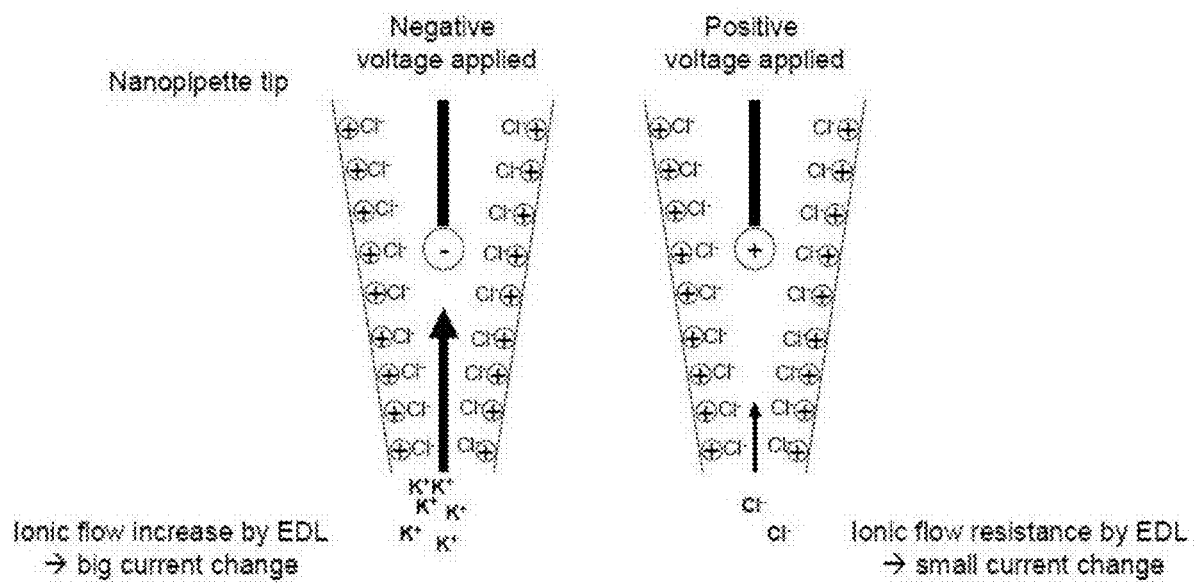
FIG. 9 is a schematic drawing showing changes in ionic flow that result from the formation of an electrical double layer (EDL) on the inner surface of the nanopipette. On the left, ionic flow increase by an electrical double layer (EDL) is shown, resulting in a large current change. On the right side, with positive voltage applied, there is illustrated ionic flow resistance by EDL, leading to a small current change. The circled + is positive surface charge. As a result of the surface charge an electrical double layer (EDL) of Cl— is formed. As a result the nanopipette biosensor is partially ion permselective and a larger change in current will be observed when negative voltage is applied due to the EDL.

Evident current changes of 10% or more were observed in two of the anti-human IL-10 IgG nanopipette biosensor experiments after adding human IL-10. As shown in FIG. 9, experiment 080205 showed a large change in the negative ionic current response and a small but significant change in the positive current response for the anti-human IL-10 IgG functionalized nanopipette. The same negative control used in earlier experiments was used for these experiments.

Table Summarizing Nanopipette Measurement Results

Of the seven specific binding experiments performed four showed significant change, one was ambiguous and two remained unchanged.

| Experiment | Normalized Current Change (positive/negative) | Indication of Specific Binding |
|---|---|---|
| 071206 | 0 | − |
| 080110 | 0/20-30% | + |
| 080112 (FIG. 6) | 10%/25% | + |
| 080131 | ?/5% | +/− ? |
| 080205 (FIG. 7) | 5%/20% | + |
| 080214° | 2%/10% | + |
| 080214b | ?/0 | − |

Nanopipette Biosensor Limit of Detection (LOD)

In an attempt to investigate nanopipette biosensor limit of detection different amounts of IL-10 were added four times (FIG. 8). The current profile changed at the lowest concentration of 4 ng/mL for anti-human IL-10 IgG nanopipette but also for the negative control. For the anti-human IL-10 IgG functionalized pipette the current change was not as big after a concentration of 0.4 µg/mL IL-10.

Selectivity, Sensitivity and Robustness

Out of the seven experiments performed four indicated specific binding, one had unclear results and two showed no specific binding. The nanopipette biosensors have repeatedly and with two different cancer biomarkers as target molecules been shown to be selective but not very robust and more experiments need to be performed.

To investigate the nanopipette's sensitivity and the limit of detection (LOD), additional experiments were carried out. In order to ascertain limit of detection, the first addition of analyte should not have changed the current, but it did. It was established with this experiment that a change was only observed for addition to the concentration of 4 ng/mL of IL-10 and that the limit of detection for nanopipette biosensors could be smaller than ~4 ng/mL. If this is true, the nanopipette biosensor technology is approximately within the same detection order range as the plasma concentration level of IL-10 in cancer patients and could be used for this aim since IL-10 plasma concentrations of ~8 ng/mL have been measured with ELISA for cancer-bearing patients. It should be noted that measuring clean sample of target protein and target protein in plasma could affect LOD for any technique. Current changes upon analyte addition in negative control were also seen in this experiment which makes it difficult to draw any conclusions from these results. A blank addition in the beginning without analyte could have helped in the data analysis here.

A trend seen in the nanopipette experiments was that the negative peak current profile changed more than the positive equivalent. One contributing cause to this trend may be the ionic permselectivity caused by an electric double layer (EDL) predicted by Wei et al., see FIG. 9. When negative voltage was applied to the nanopipette, a flow of potassium ions went through the tip. This ion current will be enhanced if the EDL is also negative. On the other hand, positive applied voltage to the nanopipette tip results in negative chloride ions passing through the pore. This flow is smaller due to repelling electrostatic forces from the negatively charged EDL. The EDL is part of a rectification effect that functionalization of the nanopipette will create. It is important to measure currents in both positive and negative modes.

Given the data presented here, it can be seen that further optimization of the surface chemistry can be done. Some experiments have suggested that cutting incubation time for Protein A/G and antibodies is a possibility. This could further speed up the preparation process. In addition, the concentration of immobilized antibodies should be investigated more and possibly optimized. For the glass slide experiment a Protein A/G-antibody ratio of 1:5 was used successfully, however due to quantity constraints the same ratio for the nanopipette experiments were about 1:0.5.

By using several pipettes in a flow chamber multiplex of the nanopipette biosensor technology could be made a reality. Serum or other samples with multiple analytes could move through the flow chamber and parallel target detection by differentiating functionalized nanopipette biosensors as predicted.

In this example, antibodies were immobilized onto the nanopipette surface and antigens were added to the electrolyte bath. With a different surface chemistry reversed detection could be applied if antigens were immobilized to the surface and corresponding antibodies were added to the detection bath. So called antibody sandwich assays, with primary antibody-antigen-secondary antibody binding structure, is also a plausible approach.

Naturally, nanopipette biosensors are not only applicable to antibodies and cancer markers but to other probe/target molecules as well. Cytokines with their corresponding receptors are additional interaction pairs to investigate.

In repeated voltage clamp experiments, the nanopipette biosensors proved to specifically detect antigen molecules in real-time at a concentration of 4 µg/mL. The antigen molecules used were considerably smaller than antibodies (VEGF and IL-10 ~19 kDa compared to 150 kDa for most antibodies), showing that the system is sensitive. In an attempt to establish limit of detection (LOD), a current profile change was observed at a concentration of 4 ng/mL of analyte. Since this was the smallest concentration used in a nanopipette biosensor experiment so far, LOD is still unknown but believed to be <4 ng/mL. Compared to state-of-the-art protein analysis techniques such as ELISA and SPR, the nanopipette biosensor technology platform holds future application potential with further development.

REFERENCES

1. Deamer, D. W. and M. Akeson, Nanopores and nucleic acids: prospects for ultrarapid sequencing, *Trends Biotechnol.* 18:147-51 (2000)
2. Deamer, D. W. and D. Branton, Characterization of Nucleic Acids by Nanopore Analysis, Acc. *Chem. Res.* 35:817-25 (2002)
3. Kasianowicz J. J., E. Brandin, D. Branton D. W. Deamer, Characterization of individual polynucleotide molecules using a membrane channel, *PNAS* 93:13770-3 (1996)
4. Li J., M. Gershow, D. Stein, E. Brandin, J. A. Golovchenko, DNA molecules and configurations in a solid state nanopore microscope, *Nat. Mater.* 2:611-5 (2003)
5. Loweth, C. J, W. B. Caldwell, X. Peng, A. P. Alivisatos, and P. G. Schultz, DNA-based Assembly of Gold Nanocrystals, *Agnew. Chem. Int. Ed.* 38:1808-1812 (1999)
6. Peng, X. G., L. Manna, W. D. Yang, J. Wickham, E. Scher, A. Kadavanich, A. P. Alivisatos, "Shape control of CdSe nanocrystals," *Nature* 404, 59 (2000)
7. Puntes V. F., K. M. Krishnan and A. P. Alivisatos, "Colloidal nanocrystal shape and size control: the case of cobalt Science," *Science* 291, 5511: 2115-2117 (2001)
8. Sakmann, B. and E. Neher, Single Channel Recording, 2nd Edition, Plenum Press, New York (1995)
9. Sun, S., C. B. Murray, D. Weller, L. Folks and A. Moser, "Monodisperse FePt nanoparticles and ferromagnetic FePt nanocrystal superlattices," *Science* 287, 5460:1989-92 (2000)

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A device for specific detection of a plurality of analytes in a sample, the device comprising:
   a flow chamber comprising:
   a plurality of capillary nanopipettes,
      each capillary nanopipette comprising:
         a tip with a 10 nm-100 nm diameter, wherein the tip is positioned in the flow chamber for contacting a sample flowing through the flow chamber;
         a coating of an analyte-binding peptide at the tip, wherein the analyte-binding peptide specifically binds to an analyte;
         an electrode positioned in an interior volume of the capillary nanopipette and in contact with an electrolyte solution contained in the interior volume,
   a current detecting circuit connected to the electrode in each capillary nanopipette for detecting current through the tip;
   an electrode positioned in the flow chamber outside of the nanopipettes for contacting the sample and connected to the current detecting circuit;
   an amplifier connected to each of the electrodes in the capillary nanopipettes and configured to apply an alternating voltage to each of the electrodes thereby producing positive and negative currents, and the current detecting circuit configured to detect both of the positive and negative currents,
   wherein upon binding of an analyte in the sample to the tip of a capillary nanopipette both the positive and negative currents from the capillary nanopipette detected by the current detecting circuit are reduced.

2. The device of claim 1, wherein a first capillary nanopipette of the plurality of capillary nanopipettes comprises a first analyte-binding peptide and a second capillary nanopipette of the plurality of capillary nanopipettes comprises a second analyte-binding peptide, wherein the first and second analyte-binding peptides specifically bind different analytes.

3. The device of claim 2, wherein the first and second analyte-binding peptides are selected from the group consisting of: an antibody, an antigen, a hormone receptor, and an enzyme.

4. The device of claim 1, wherein the plurality of capillary nanopipettes are glass capillary nanopipettes.

5. The device of claim 1, wherein the plurality of capillary nanopipettes are quartz capillary nanopipettes.

6. The device of claim 1, wherein the tip of each capillary nanopipette is coated with a polymer and wherein the polymer comprises poly-L-Lysine.

7. The device of claim 1, wherein the analyte-binding peptide comprises an antibody.

8. The device of claim 1, wherein the amplifier is configured to apply a sinusoidal alternating voltage.

9. The device of claim 8, wherein the alternating voltage alternates at between 0.5 and 10 Hz.

10. The device of claim 1, wherein the analyte-binding peptide is attached to the tip by an NHS (N-hydroxysuccinimide) coupling agent.

11. The device of claim 1, wherein the plurality of capillary nanopipettes are quartz capillary nanopipettes and wherein the tip of each capillary nanopipette is coated with a polymer and wherein the polymer comprises poly-L-Lysine.

12. The device of claim 1, wherein the plurality of capillary nanopipettes are glass capillary nanopipettes or quartz capillary nanopipettes and wherein the analyte-binding peptide comprises an antibody.

13. The device of claim 1, comprising a plurality of amplifiers wherein each electrode in each capillary nanopipette is connected to a different amplifier.

* * * * *